United States Patent [19]

Roque

[11] 4,121,907

[45] Oct. 24, 1978

[54] SAMPLE HANDLING SYSTEM

[75] Inventor: Leonard Roque, Miami, Fla.

[73] Assignee: Coulter Electronics, Inc., Hialeah, Fla.

[21] Appl. No.: 805,715

[22] Filed: Jun. 13, 1977

[51] Int. Cl.² .............................................. G01N 1/14
[52] U.S. Cl. ............................... 356/246; 73/425.4 R; 422/55
[58] Field of Search ................. 23/230 R, 253 R, 259; 356/246; 73/425.4 R, 425.6

[56] References Cited

U.S. PATENT DOCUMENTS

| | | | |
|---|---|---|---|
| 3,525,592 | 8/1970 | Buckley | 23/259 X |
| 3,557,077 | 1/1971 | Brundfeldt et al. | 23/259 X |
| 3,567,390 | 3/1971 | Rothermel | 23/259 X |
| 3,607,092 | 9/1971 | Neff et al. | 23/253 R |
| 3,948,607 | 4/1976 | Atwood et al. | 23/253 X |
| 3,976,429 | 8/1976 | Ginsberg | 23/230 R |

*Primary Examiner*—R.E. Serwin

*Attorney, Agent, or Firm*—Silverman, Cass & Singer, Ltd.

[57] ABSTRACT

A pneumatic/hydraulic sample handling system which includes a source of alternative vacuum and pressure, a normally closed, selectively operable valve to permit flow through the system withdrawing a known aliquot from a source of sample, directing said aliquot to a vessel for analysis, an isolation chamber disposed in the flow path between said source of vacuum and pressure and said vessel and having inlets respectively coupled into the flow path and a relief valve arranged between the isolation chamber and said source of vacuum and pressure, said isolation chamber having an outlet, a conduit coupling said outlet to a waste depositary, pressure differential sensitive check valve interposed in said conduit between said outlet and said waste depositary, and a microcomputer circuit arranged to control the operation of said system in accordance with a predetermined procedure.

15 Claims, 6 Drawing Figures

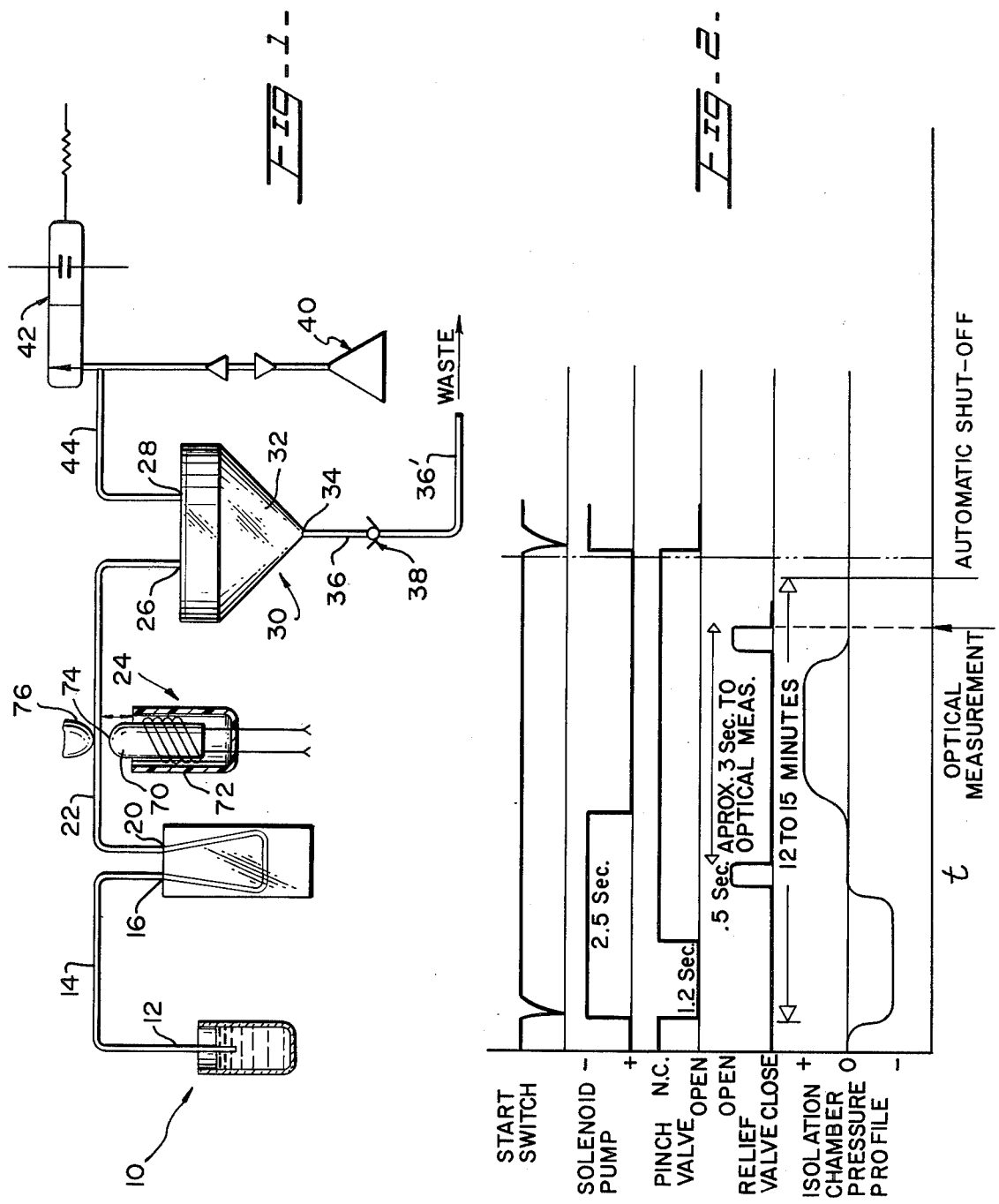

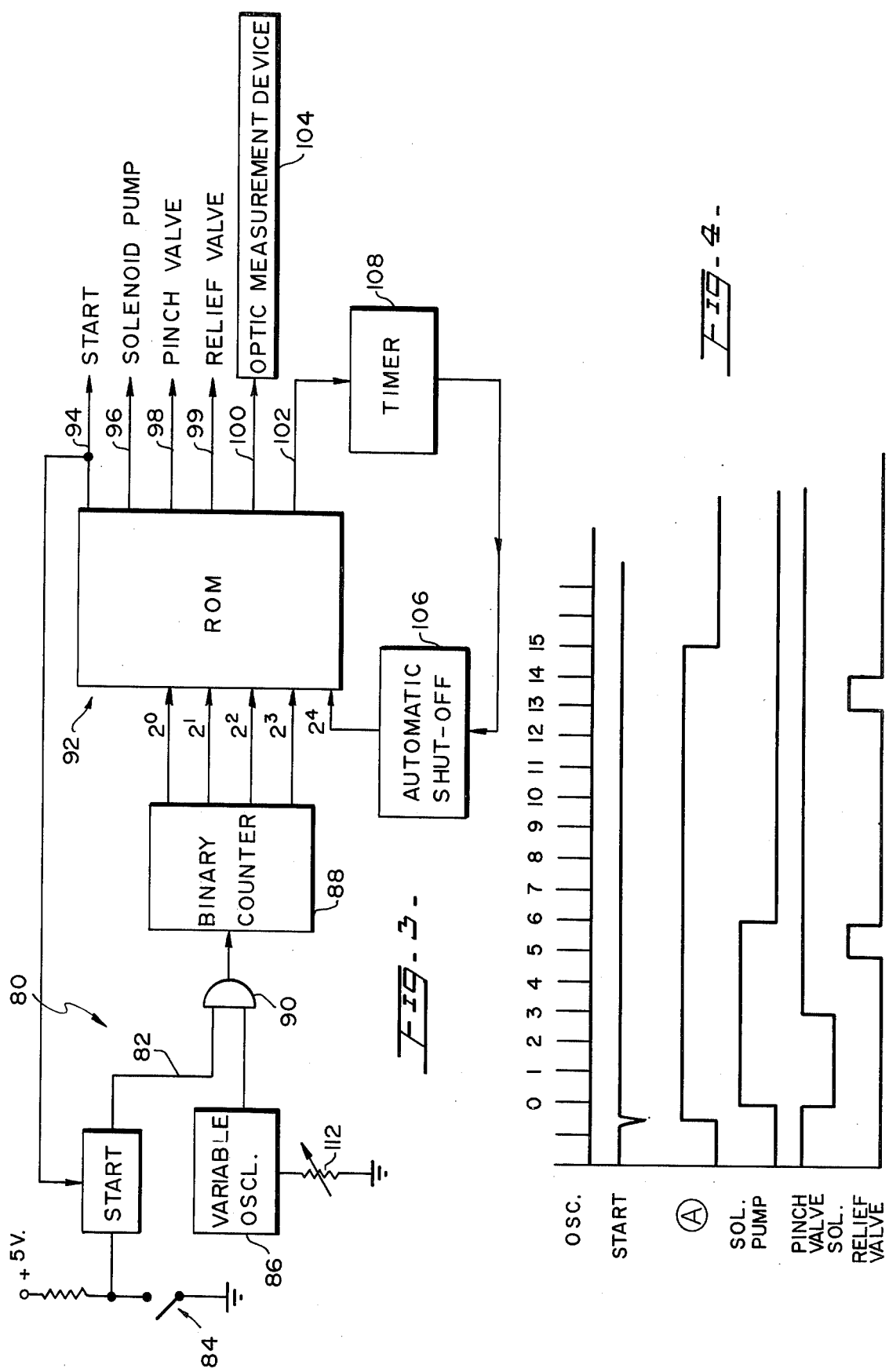

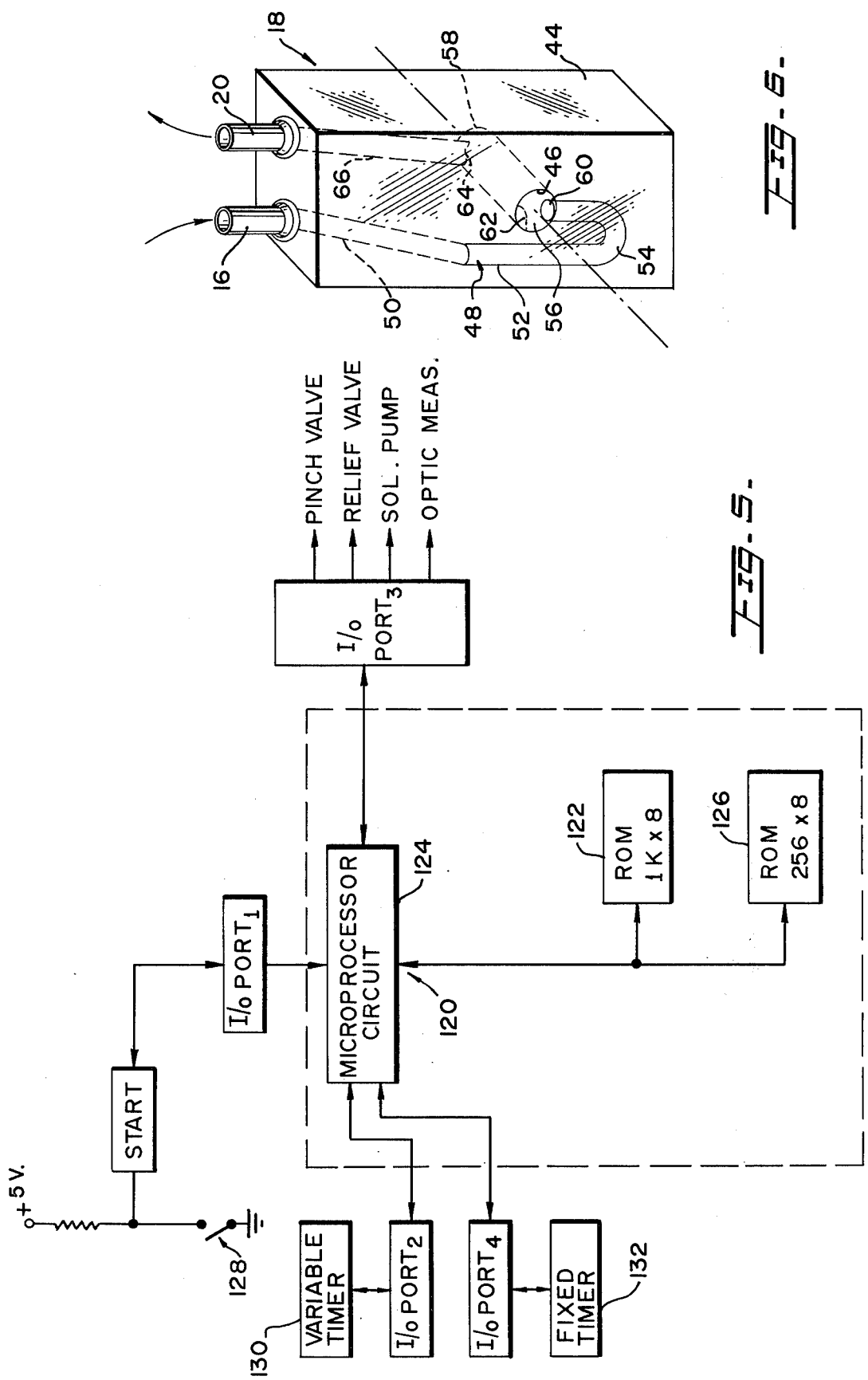

SAMPLE HANDLING SYSTEM

BACKGROUND OF THE INVENTION

This invention relates generally to sample handling systems for automatic and semiautomatic fluid analyzing systems and is concerned particularly with the provision of a system utilizing pneumatics and hydraulics to effect aliquot sample withdrawal and movement, with an isolation chamber provided to function as a buffer between the pneumatics and hydraulics for preventing surges, and as well, to provide a microcomputer as a control for operation of said system in conjunction with the optical analysis of the successive sample aliquots in the system which includes a flow cell.

Automatic and/or semi automatically operated testing apparatus require the taking of aliquot portions of a liquid sample to be tested, transferring these aliquots to a testing station, holding each aliquot at the testing station for the duration of the test and disposing of the tested aliquot from the testing station to a waste receiving location.

Successful operation of the testing apparatus demands careful control of the aliquot volume and its movement through the system. Pneumatic means such as vacuum and/or air pressure is utilized alone or in conjunction with the use of hydraulics can be employed to draw and to move the aliquot.

One problem encountered in the use of sample handling systems involving both pneumatics and hydraulics is occasioned by the generation of turbulence in the liquid causally related at least in part by the abrupt changes in pressure. Another involves the danger of carryover from one body of liquid occasioned by the relative relationship of the pneumatic and hydraulic systems, and their possible overlap. Turbulence sufficient to draw bubbles or to cause bubbles to be generated, produces erroneous results since the bubbles may be trapped in the test chamber of the testing apparatus, interfering with passage of the light beam.

Accordingly, it is desired to provide means to serve as a buffer between the pneumatic and hydraulic systems so that pressure changes occasioned in moving the liquid bodies can be applied through such means rather than directly to the conduits through which the liquid bodies travel, whereby smooth flow is obtained throughout the system and surges eliminated.

Another problem encountered may be attributable to the operation of the system at a slow rate, an often suggested and adopted solution for avoidance of turbulence in flowing liquid systems. Here the flow rate elected may be too slow, forming an optically interferent dead zone interior of the flow cell at the testing station in the general scheme of the system concerned.

Accordingly, the invention further provides a flow cell construction having a path arranged to improve the rate of flow through the flow cell.

SUMMARY OF THE INVENTION

A sample handling system of the type having a hydraulic liquid flow system, a pneumatic flow system operating to move the liquid of the hydraulic flow system and means interposed between said hydraulic system and said pneumatic system for isolating one system from the other.

The hydraulic flow system includes a liquid flow conduit, flow cell means for retaining a portion of the liquid and pinch valve means operable to control flow through said hydraulic system.

The pneumatic system includes a source of alternating pressure and vacuum, conduit means leading from said source to a delivery location and relief valve means operating selectively to connect said delivery location to atmospheric pressure between cycles of pressure and vacuum applied thereto.

The isolating means comprise a chamber having a pair of inlet ports and an outlet port, one inlet port coupled to said hydraulic system downstream of said pinch valve means and the other inlet port coupled to said pneumatic conduit upstream of the relief valve means and check valve means coupled to the outlet port between said outlet port and a waste delivery location.

Computer means are provided to coordinate and to control the activities of the operable elements of said system.

BRIEF DESCRIPTION OF THE DRAWINGS

FIG. 1 is a schematic flow representation of the sample handling system according to the invention;

FIG. 2 is a graphical representation of the operation of the system illustrated in FIG. 1, in the form of a time chart.

FIG. 3 is a schematic representation of the electrical control array of the system represented in FIGS. 1 and 2.

FIG. 4 is a schematic representation of the operation of the control array illustrated in FIG. 3, in the form of a time chart.

FIG. 5 is a schematic representation of a modified control array.

FIG. 6 is a perspective view of an optical test flow cell used in the system of FIG. 1.

DESCRIPTION OF PREFERRED EMBODIMENT

Briefly, the invention provides a sample handling system for testing apparatus of the automatic or semiautomatic type wherein a combination of an hydraulic and a pneumatic system is employed to draw a sample aliquot from a sample source, pass that aliquot into a test flow cell and hold same therein for testing purposes. A pneumatic system including a source of alternating vacuum and pressure operates upon the hydraulic system to move the liquid therein, with an intermediate or isolation chamber separating the hydraulic system from the pneumatic system to prevent surges and turbulence during the operation thereof. The pneumatic system includes means for bringing the isolation chamber to atmospheric pressure between cycles of vacuum and pressure applied threto. The isolation chamber is coupled through check valve means to a waste delivery location. The respective systems are controlled to operate in accordance with a timed program so that repetitive samplings and tests can be made and completed respectively, with means provided for automatically disabling the operation after a predetermined elapse of time.

Referring now to the drawing, the sample handling system in accordance with the invention is represented schematically in FIG. 1, and is designated generally by reference character 10. The system 10 is described herein as operational in automatic or semi-automatic apparatus utilizing optical ultraviolet kinetic measurement or standard end point chemical analytical techniques.

The sample handling system 10 comprises a pneumatic system including a sample probe 12, coupled via conduit 14 to the inlet 16 of flow cell 18. Conduit 22 is coupled to the outlet 20 of flow cell 18 and leads past solenoid operated pinch valve 24 to one inlet port 26 of isolation chamber 30. The isolation chamber 30 is provided with a conical floor 32 tapered to outlet port 34. Conduit 36 is coupled to outlet port 34 and leads to check valve assembly 38 from whence conduit 36' leads to a waste delivery location. Conduits 14, 22, 36 and 36' preferably are formed of flexible chemically resistant tubing with conduit 22 being required to be flexible and resilient.

The sample handling system 10 further includes a pneumatic system, including a solenoid pump 40 functioning as an alternating source of vacuum and of pressure, and a relief valve 42, each coupled in parallel by conduit 44 to the other inlet port 28 of isolation chamber 30.

The isolation chamber 30 serves to bridge the hydraulic and the pneumatic systems, functioning as a buffer therebetween to prevent surges occasioned by the alternating vacuum/pressure operation of said pneumatic system, according to the program required.

The flow cell 18 comprises a body 44 having an inlet tube 16, a horizontally oriented examination chamber 46. The conduit 48 includes a diagonal portion 50, a generally linear portion 52 and a U-portion 54 coupled to the chamber 46 adjacent one end thereof. Chamber 46 is of generally cylindrical configuration and has a pair of parallel windows 56, 58 at opposite ends thereof. The U-portion 54 of conduit 48 is oriented to enable the liquid entering the chamber 46 at 60 to sweep across window 56 thus restricting any dead-zone formed, as represented by reference character 62, from interfering with a beam of light passing through the chamber 46. The outlet 64 of the chamber 46 is oriented 180° from the inlet 56 so that the liquid sweeps across window 58 to exit the chamber 46, entering vertical conduit 66 leading to the outlet port 68. The optical path defined between windows 56 and 58 preferably is 10 mm. in length. The relative arrangement of the portions of the flow path through flow cell 18 reduces the occurrence of bubbles, turbulence, etc. and establishes an unobstructed optical path for examination purposes.

The conduit 22 is coupled to the outlet port 68 and leads past solenoid operated pinch valve 24 which operates thereupon, and terminates at the inlet port 26 of isolation chamber 30. The solenoid operated pinch valve 24 has a plunger 70 and a body or housing 72. The plunger 70 is reciprocable between a position within the body or housing 72 and a position extended outward therefrom. The plunger 70 has a free end 74 which bears upon conduit 22 when the plunger 70 is extended outwardly of the housing 72 collapsing said conduit 22 against a backup member 76, shutting off flow through said conduit 22.

A check valve assembly 38 is located on the output side of the isolation chamber 30 and is of the so-called "duck-bill" type, activated only when there is a pressure differential, *in one direction*.

A relief valve 42 is provided for the purpose of normalizing the pressure interior of the isolation chamber 30 between cycles. The source of vacuum and of pressure for the system 10 comprises a solenoid pump 40. Pump 40 is formed of corrosion resistent material. Pump 40 is operable to provide either fluid pressure (air pressure) or vacuum condition within the isolation chamber 30. Vacuum causes the liquid sample to be drawn from the source of sample through the sample probe 12.

The control circuitry for operating the sample handling system 10 is represented in the schematic of FIG. 3 and includes a timing circuit 80 which is enabled upon generation of a start signal 82 produced when the start switch 84 is closed. The timing circuit 80 further includes a variable oscillator 86 with frequencies between 0.5 and 0.7 Hertz per second. Oscillator 86 controls the volume of the aliquot drawn by the system 10 because the oscillator 86 controls the time during which the solenoid pinch valve 24 remains open, the volume being changeable in inverse relation to the frequency of the oscillator. The timing circuit 80 also includes a binary counter 88. The oscillator signal from oscillator 80 is gated at 90 with the start signal 82 to drive the binary counter 88. Binary counter 88 has a plurality of parallel outputs to the ROM (read only memory) microcomputer 92 from which parallel outputs 94, 96, 98 and 99 feed respectively back to the starting circuit 80, to the solenoid pump 40, to the solenoid pinch valve 24 and to relief valve 42. Outputs 100 and 102 lead respectively to the optical type measuring device 104 and, through timer 108, to automatic shut-off 106 for the binary counter 88, the automatic shut-off 106 being essentially a transistor switch.

The timer 108 is driven by ROM 92, which is programmed in such a way that it will provide the right binary timing cycle, which is once each 16 outputs from oscillator 88, to supply pulses and sequences for the actuation of the different hydraulic and pneumatic control elements in system 10. The timer 108 receives a signal every binary counter signal, which is once every sixteen outputs from the oscillator 88. This signal results in an enable signal directed along lead 102 to the timer 108. The timer 108 has a resistive-capacitor combination which produces the time constant sufficient to produce an output signal roughly every fifteen minutes subsequent to the enable signal.

The output of the automatic shut-off circuit is returned to the ROM 92 to drive the $2^4$ bit in the ROM 92 from "0" state to reset the timer again to start the 15 minute cycle again.

So long as there is a series of start signals 82 with less than 15 minute interval therebetween, the timer 108 never will get to the end of its timing cycle of 15 minutes to trigger the automatic shut-off 106 until there has been a total elapse of time of approximately 15 minutes plus 16 bits from the last initiated start signal 82. The output from timer 108 then goes through the automatic shut off 106 to cause the $2^4$ input bit line of the ROM 92 to change state whereby to initiate the automatic shut-off program cycle of the ROM 92.

A variable resistor 112 for the oscillator 88 is provided to change the rate of output pulses of the oscillator 88 so as to change the elasped time of the binary counter cycle and thus change the operation of the ROM. Accordingly, calibration for the total sample withdrawn from the source may be effected by adjusting the variable resistor 112.

Referring to the timing chart of FIG. 4, the start switch 84 is closed providing the start signal 82. Simultaneously, the plunger 70 of solenoid pinch valve 24 is withdrawn into the housing 72 permitting flow through the conduit 22. At the same time, solenoid pump 40 is activated to draw a vacuum within the isolation chamber 30. The solenoid pinch valve 24 remains open for approximately 1.2 seconds. The solenoid pump 40 operates for approximately 2.5 seconds. After the solenoid pinch valve 24 returns to its normally closed condition with the plunger 70 extending from the housing 72, the relief valve 42 is shifted from its normally closed condition to open condition. As a result communication is established to the atmosphere, causing the isolation chamber 30 to lose its vacuum and return to atmospheric pressure. After about one half second, the relief valve 42 is closed. The solenoid pump changes state to put out a positive pressure. The isolation chamber 30 receives positive pressure forcing the liquid therein through outlet 34, through the check valve 38 to the waste delivery location, W. About 3 seconds subsequent to the aforementioned closing, the relief valve 42 once again is opened, bringing the interior of the isolation chamber 30 back to atmospheric pressure.

Now the optical measurements can take place. It is possible earlier to perform the optical measurement but since the flow cell is temperature regulated, and a finite time is required for the sample to reach proper temperature within the flow cell 18, and particularly within chamber 46 thereof. The opening and closing of the various solenoid operated elements causes some electrical interference which may be adverse to the accuracy of the optical measurement so that simultaneous operation of the solenoids (i.e., valve 24, pump 40) and the optical measurement is avoided.

As soon as the optical measurement is completed, the start switch 84 is activated to commence a new cycle. If there is no initiation of a new start signal, the system 10 enters the automatic shut-off mode, causing one more partial cycle, in which air is drawn through the system and the system is left with the solenoid operated pinch valve in open condition. The next cycle of operation may be initiated with operation of the solenoid pump without activating the pinch valve.

Referring to FIG. 5, a microprocessor circuit 120 can be substituted for the binary counter 88 and the ROM 92 represented in FIG. 3. The microprocessor circuit 120 includes a ROM 122 coupled to microprocessor 124 with a RAM (random access memory) 126 also being coupled to the microprocessor 124. The operation is similar to the earlier discussed operation. The chain of events previously described essentially is the same.

A start command is generated by closing a switch 128, the start command passing through bidirectional I/o port 1. As a part of the program of the microprocessor 124 a finite chain of events must occur as far as sample handling is concerned. The variable timer 130 issues pulses at selected rate to microprocessor 124. Dependent upon the pulse number and related to the timing diagram, with either the solenoid operated pinch valve 24 is caused to open, the relief valve 42 closed, the pump 40 operates or the optical measurements are made. In the system of FIG. 5 a fixed timer 132 has replaced the timer 108 and automatic shut off 106, and is connected to the I/o port 4. In this case the timer 132 is incremental and the microprocessor 124 goes through an automatic shutdown procedure to which reference previously was made.

The ROM functions as a program while the RAM is a work area. The microprocessor has complete control over the decisional process regarding sample handling. The timing relationship between the signals seen at the output of I/o port 3 is the same as those shown in FIG. 3. Likewise, the start, variable and fixed timer functions also remain basically the same as previously described.

The variable timer 30, in contrast with the timing circuit issuing continuous plural pulses, issues but one pulse. The microprocessor receives that one pulse and adds a numeric "one" to a specific location in the RAM. The microprocessor will reset the variable timer 30 and allow it to time out and issue a second pulse. This second pulse will be received and referred back to the same memory location in the random access memory location in the random access memory (RAM) and increment that by one.

When the memory location increments equal a numerical four, the pinch valve 24 is actuated. Feeding of successive pulses to that memory location is continued. When it reaches a numerical eight, the signal to deactivate the pinch valve is issued.

The microprocessor 124 compares the number of pulses stored in the RAM to a number which is stored in the ROM to determine the point in time at which the performance 1 of a specific event is expected. To some extent, the RAM effectively replaces the binary counter or a portion of the binary counter's output to convert the variable timer's output into a recognized counting mode. The microprocessor circuit (RAM and ROM) could be termed a "microcomputer."

What I claim is:

1. A sample handling system for drawing successive aliquot volumes from a source of liquid sample, moving said aliquots singly to and through a test cell and thence to a waste depositary subsequent to the completion of the test, said system comprising:
   a hydraulic liquid flow system for defining a flow path,
   a pneumatic system operable upon said hydraulic system for moving the liquid along said flow path,
   an isolation chamber intermediate said hydraulic and pneumatic systems and having a pair of inlet ports respectively coupled to said hydraulic and pneumatic systems and an outlet port coupled to a waste depositary,
   said pneumatic system including means for generating periodic alternating pressure and vacuum, and means coupling said generating means to said isolation chamber, means coupled communicatively between said generating means and said isolation chamber for establishing an atmospheric pressure condition in said isolation chamber between each application of pressure and vacuum to said isolation chamber, and
   control circuit means for operating said systems according to a programmed sequence.

2. The system as claimed in claim 1 in which said hydraulic system includes probe means immersible in the source of sample, flow cell means for receiving and holding an aliquot sample, conduit means coupled between said probe means and said flow cell means and leading therefrom to said isolation chamber, and valve means selectively operable to pass liquid along said system from said source of sample through said flow cell to said isolation chamber.

3. The system as claimed in claim 2 in which said last mentioned valve means comprise a solenoid operated pinch valve.

4. The system as claimed in claim 2 in which said generating means comprise a solenoid operated pump.

5. The system as claimed in claim 3 in which said generating means comprise a solenoid pump.

6. The system as claimed in claim 2 in which vacuum is applied to said isolation chamber and simultaneously, the valve means is operable to permit flow along said flow path.

7. The system as claimed in claim 6 in which pressure is applied to said isolation chamber to direct the content thereof to a waste delivery depositary.

8. The system as claimed in claim 7 in which said means for establishing atmospheric pressure condition in said isolation chamber comprise a relief valve coupled to said isolation chamber on the generating means side thereof.

9. The system as claimed in claim 1 in which said control circuit means comprise means for generating a plurality of pulses, means for receiving said pulses and means for correlating the number of pulses received to the operation of said pneumatic and hydraulic systems in a programmed sequence.

10. The system as claimed in claim 9 in which said means for generating a plurality of pulses comprise a variable oscillator.

11. The system as claimed in claim 9 in which said means for receiving said pulses comprise a computer, said computer having an automatic shut off mode.

12. The system as claimed in claim 11 in which said computer comprises a binary counter coupled to a read-only-memory, the outputs thereof being coupled operatively to said systems.

13. The system as claimed in claim 11 in which said computer comprises a microprocessor circuit, variable timer means and fixed timer means respectively coupled to said microprocessor circuit, read-only-memory means and random-access-memory means coupled in parallel to said microprocessor circuit and means coupling said microprocessor circuit to said systems for operating same.

14. The system as claimed in claim 2 in which said valve means comprise a normally closed solenoid operated pinch valve operable upon the flow path and said control means operates to open said pinch valve simultaneously with the application of vacuum to said isolation chamber.

15. The system as claimed in claim 1 in which said test cell comprises a flow cell, said flow cell having a body, said body having an interior chamber, said interior chamber having a pair of opposite parallel windows, inlet and outlet means, conduit means leading between said inlet and outlet means to said chamber respectively, said conduit means leading to said chamber having a U-shaped portion communicating directly to said chamber whereby liquid is swept across the window adjacent entry to said chamber, said chamber being arranged oriented to define an unobstructed optical path axially through the chamber.

* * * * *

UNITED STATES PATENT AND TRADEMARK OFFICE
CERTIFICATE OF CORRECTION

PATENT NO. : 4,121,907
DATED : October 24, 1978
INVENTOR(S) : LEONARD ROQUE

It is certified that error appears in the above-identified patent and that said Letters Patent are hereby corrected as shown below:

Column 4, line 43, after '"O" state' insert

-- to a "1" state --

Signed and Sealed this

Twenty-fifth Day of September 1979

[SEAL]

*Attest:*

*Attesting Officer*

LUTRELLE F. PARKER
*Acting Commissioner of Patents and Trademarks*